United States Patent [19]

Miyazaki et al.

[11] Patent Number: 5,440,019
[45] Date of Patent: Aug. 8, 1995

[54] PROCESSES OF PRODUCING AMYLASE INHIBITORS

[75] Inventors: Toshiyuki Miyazaki; Toshihisa Morimoto, both of Saitama; Ryuji Murayama, Hyogo, all of Japan

[73] Assignees: Nisshin Flour Milling Co., Ltd., Tokyo; Nagata Sangyo Co., Ltd., Hyogo, both of Japan

[21] Appl. No.: 286,176

[22] Filed: Aug. 5, 1994

[30] Foreign Application Priority Data

Aug. 6, 1993 [JP] Japan ................. 5-213500

[51] Int. Cl.⁶ ................. C07K 1/32; C07K 14/415
[52] U.S. Cl. ................. 530/374; 530/375; 530/415
[58] Field of Search ............. 530/374, 375, 415, 420, 530/423, 424, 425

[56] References Cited

U.S. PATENT DOCUMENTS

| | | | |
|---|---|---|---|
| 2,379,929 | 7/1945 | Rushton | 530/420 |
| 3,898,160 | 8/1975 | Finley | 530/400 |
| 3,944,537 | 3/1976 | Saunders et al. | 426/321 |
| 3,950,319 | 4/1976 | Schmidt et al. | 530/374 |
| 4,043,990 | 8/1977 | Melachouris | 530/415 |
| 4,806,626 | 2/1989 | Maeda et al. | 530/375 |
| 5,084,275 | 1/1992 | Maeda et al. | 530/375 |
| 5,093,315 | 3/1992 | Maeda et al. | 514/2 |
| 5,332,803 | 7/1994 | Miyazaki et al. | 530/375 |

FOREIGN PATENT DOCUMENTS 0567088 10/1993 European Pat. Off.

OTHER PUBLICATIONS

Journal of Food Biochemistry, vol. 1, 1977, pp. 385–401, Gramm, et al., "Purification and Characterization of Alpha-Amylase Inhibitors in Wheat".
Derwent Abstract of Japanese Patent Application 63-248,389 (Oct. 14, 1988).
Eur. J. Biochem, 183, Rosa Sanchez-Monge, et al., "New Dimeric Inhibitor of Heterologous α-Amylases Encoded by a Duplicated Gene in the Short Arm of Chromosome 3B of Wheat (Triticum Aestivum L)", 1989, pp. 37–40.
Phytochemistry, vol. 20, No. 8, Nizar Kashlan, et al., "The Complete Amino Acid Sequence of a Major Wheat Protein Inhibitor of α-Amylase", 1981, pp. 1781–1784.

*Primary Examiner*—Jeffrey E. Russel
*Attorney, Agent, or Firm*—Oblon, Spivak, McClelland, Maier & Neustadt

[57] ABSTRACT

A process of producing an amylase inhibitor from an amylase inhibitor-containing solution extracted from wheat flour, etc with water, a dilute acid, a dilute alkali or from an amylase inhibitor-containing starch waste solution, by utilization of an adsorption of the amylase inhibitor on a calcium phosphate gel, while removing impure proteins contained in the solution. The process can produce in economy and high yields the amylase inhibitor having a very high amylase inhibitory activity but no or very little trypsin inhibitory activity.

6 Claims, No Drawings

5,440,019

PROCESSES OF PRODUCING AMYLASE INHIBITORS

FIELD OF THE INVENTION

This invention relates to processes of producing an amylase inhibitor from wheat, wheat flour or wheat gluten or from a starch waste liquid and also to the application of such amylase inhibitor as a medicine or food.

BACKGROUND OF THE INVENTION

The amylase inhibitors of wheat origin have been investigated (see, Phytochemistry, Vol. 20, No. 8, pp. 1781–1784; Eur. J. Blochem. 183, 37–40 (1989)).

U.S. Pat. No. 3,950,319 discloses that the amylase inhibitor extracted from wheat with water, an acid or an aqueous alcohol is used for the treatment of diabetes, obesity and the like.

The prior amylase inhibitors of wheat origin have not achieved such effect as expected when orally administered, which has the disadvantages of high cost and reduced inhibition of digestion to glucose, particularly for the digestion of heat cooked starch such as cooked rice.

Under such situation, a process has been sought of preparing in economy an amylase inhibitor which is effective in an oral administration for the digestion of heat cooked starch.

Japanese Patent Kokai Hei 5-301898 (corresponding to EPA 0567088 A2, Nisshin Flour Milling Co., Ltd.) discloses that the amylase inhibitors having a high amylase inhibitory activity but substantially no trypsin inhibitory activity can be produced by a process which comprises extracting wheat, wheat flour or wheat gluten with water, a dilute acid, a dilute alkali or an aqueous alcohol; adding a polysaccharide to an extract and separating the resultant insoluble complex from the solution; dissolving or dispersing said complex in a solution, then separating the polysaccharide from the solution to collect a solution containing the amylase inhibitor; and treating the collected solution with a cation exchanger to recover the amylase inhibitor from fractions that have not been adsorbed on the cation exchanger.

SUMMARY OF THE INVENTION

An object of the invention is to provide a process of producing in economy and in high yields an amylase inhibitor having a very high amylase inhibitory activity but no or very little trypsin inhibitory activity from an extract solution of wheat, wheat flour or wheat gluten or from a starch waste solution.

Another object of the invention is to provide a process of producing such amylase inhibitor with good operability while controlling occurrence of loss even when the amount of the solution treated is much.

According to the present invention, there are provided two processes including a principal step for the formation of a calcium phosphate gel and adsorption of the amylase inhibitor thereon.

The first process of the invention comprises the steps of:

($A_1$) treating an amylase inhibitor-containing solution extracted from wheat, wheat flour or wheat gluten with water, a dilute acid, a dilute alkali or an aqueous alcohol or treating an amylase inhibitor-containing waste water washings discharged during the recovery of starch and/or gluten from wheat flour, to modify soluble impure proteins and other impurities contained therein to their insoluble solid forms, and subsequently separating and removing the solid forms;

($B_1$) adding a calcium ion and a phosphate ion to the extract solution or the waste water washings after removal of impurities obtained in step ($A_1$) to form an insoluble calcium phosphate gel while adsorbing the amylase inhibitor on the calcium phosphate gel, and subsequently separating and recovering the calcium phosphate gel containing the amylase inhibitor adsorbed thereon;

($C_1$) solubilizing the amylase inhibitor in water from said insoluble calcium phosphate to form a solution containing the amylase inhibitor; and ($D_1$) recovering the amylase inhibitor from the solution.

The second process of the invention comprises the steps of:

($A_2$) adding a calcium ion and a phosphate ion to an amylase inhibitor-containing solution extracted from wheat, wheat flour or wheat gluten with water, a dilute acid, a dilute alkali or an aqueous alcohol, or to an amylase inhibitor-containing water washings discharged during the recovery of starch and/or gluten from wheat flour to form a calcium phosphate gel while adsorbing the amylase inhibitor on the calcium phosphate gel, and subsequently separating and recovering the calcium phosphate gel containing the amylase inhibitor adsorbed thereon;

($B_2$) solubilizing the amylase inhibitor in water from said insoluble calcium phosphate gel to form a solution containing the amylase inhibitor; and ($C_2$) treating the amylase inhibitor-containing solution to modify soluble impure proteins and other impurities contained therein to their insoluble solid forms, and subsequently separating and removing said solid forms;

($D_2$) recovering the amylase inhibitor from the solution.

DETAILED DESCRIPTION OF THE INVENTION

Initially, the process steps in the first process of the invention are illustrated below.

Process Step ($A_1$)

Water is most preferable for the extraction of an amylase inhibitor-containing solution, but a dilute acid, a dilute alkali or an aqueous alcohol may be used in place of water. For the dilute acid is conveniently employed an acidic aqueous solution at a pH of about 2–6 adjusted with an inorganic acid such as hydrochloric or phosphoric acid or an organic acid such as acetic acid. For the dilute alkali is conveniently used as an alkaline aqueous solution at a pH of 8–10 adjusted with a base such as ammonia or sodium hydroxide. For the aqueous alcohol is conveniently used an aqueous alcohol solution with an alcohol concentration of about 1–50%. The alcohols used include methanol, ethanol, isopropyl alcohol and the like.

In the extraction treatment, an extract solution containing the amylase inhibitor can be obtained by extracting wheat, wheat flour or wheat gluten with a sufficient amount (usually about 3–50 times amount) of water, a dilute acid, a dilute alkali or an aqueous alcohol, while stirring usually at a temperature of about 10°–40° C. followed by removal of solids by an appropriate means such as centrifugal separation, filtration or standing.

When waste water washings are used in Step ($A_1$), the waste liquid or water washings of the dough or batter discharged during the recovery of starch and gluten from wheat flour may be used as the amylase inhibitor-containing solution. This is advantageous for efficient use of the waste liquid or water washings discharged in the production of starch and gluten by Martin's and Batter's methods which include kneading a mixture of wheat flour and water to form a dough or batter, repeatedly washing the dough with added water, separating the gluten and starch milk (gluten wash liquid) and recovering starch from the starch milk by such means as mechanical separation.

The concentration of protein contained in the extract solution or water washings containing the amylase inhibitor is adjusted to preferably 1–10 mg/ml, more preferably 2–8 mg/ml, thereby modifying soluble impure proteins and other impurities to their insoluble solid forms which are then separated and removed. Soluble impure proteins contained in the extract solution and water washings include enzyme proteins such as $\alpha$-amylase, $\beta$-amylase, proteins such as part of albumin present in unstable state, globulin or the like. Other impurities include soluble saccharides, inorganic salts, dyes or the like. Those impurities are removed from the solution by suitable treatment for removal of impurities used in Step ($A_1$).

Suitable treatments for removal of impurities include:
(i) heating the extract solution or water washings at a temperature of 70°–90° C., preferably 85°–90° C., thereby modifying heat unstable impure proteins and other impurities to their insoluble solid forms and removing said solid forms by sedimentation;
(ii) adjusting the pH of the extract solution or water washings to not greater than 4, preferably 1.5–3, allowing to stand for a certain time followed by neutralization and removing impurities such as impure proteins which are precipitating as insoluble solids; and (iii) combination of (i) and (ii).

Insoluble impurities formed by any one of the above processes (i)–(iii) are separated and removed by any process such as filtration and centrifugation. The remaining solution containing the amylase inhibitor is provided to next step ($B_1$).

Process Step ($B_1$)

In process step ($B_1$), a calcium ion and a phosphate ion are added to the solution or water washings after removal of impurities obtained in step ($A_1$), thereby to form an insoluble calcium phosphate gel while adsorbing the amylase inhibitor on the calcium phosphate gel. Subsequently, the calcium phosphate gel containing the amylase inhibitor adsorbed thereon is separated and recovered from the solution.

As a compound serving as a source of calcium ion can be used calcium hydroxide, water-soluble inorganic calcium salts such as calcium chloride and calcium nitrate, water-soluble organic calcium salts such as calcium acetate and calcium lactate. As a compound serving as a source of phosphate ion can be used phosphoric acid, water-soluble phosphates such as sodium phosphate, potassium phosphate, ammonium phosphate and the like.

For the formation of the calcium phosphate gel in step ($B_1$), it is preferable that a concentration of calcium ion in the solution constitutes 10–200%, preferably 20–120% of a protein concentration in the solution and a concentration of phosphate ion constitutes 20–100%, preferably 30–100% of the calcium ion concentration. Further, the treatment for forming the calcium phosphate gel is preferably performed at a temperature of 30°–90° C., preferably 40°–60° C. at a pH of 5–8, preferably 6–7 of the solution.

The resultant calcium phosphate gel containing the amylase inhibitor adsorbed thereon is separated and recovered by suitable means such as filtration and centrifugation and then provided to next step ($C_1$).

Process Step ($C_1$)

In this step ($C_1$), the methods for solubilizing the amylase inhibitor in water from the insoluble complex (calcium phosphate gel containing the amylase inhibitor adsorbed thereon) include (i) the method of adding acids, (ii) the method of adding water-soluble salts and (iii) the method of heating.

In the method (i), the acids used include inorganic acids such as hydrochloric acid, sulfuric acid and organic acids such as acetic acid, lactic acid. At that time, the pH is preferably adjusted to not greater than 4, specifically 1–3. In the method (ii), the water-soluble salts used include those having a strong affinity with a calcium ion, e.g. sodium sulfate, potassium sulfate, ammonium sulfate, sodium phosphate, potassium phosphate and ammonium phosphate. Preferably, the amount of water-soluble salts used is about 1–10% by weight of the solution in which insoluble complex is dispersed. In the method (iii), it is preferable that the insoluble complex is dispersed in a sufficient amount of water and a dispersion is heated at 50°–90° C., preferably 70°–85° C.

Process Step ($D_1$)

The aqueous solution containing a solubilized amylase inhibitor obtained in step ($C_1$) may be subjected, if necessary, to centrifugation, filtration or the like to remove water-insoluble impurities, and further subjected, if necessary, to microbial elimination, sterilization (e.g. heating, alcohol sterilization, filtration for microbial elimination), cation exchanger (e.g. polymer cation exchange resins, aluminum silicate or the like), desalting or concentration, and thereafter drying to produce the desired amylase inhibitor in solid form such as powders. The drying treatment may be carried out by any suitable method such as lyophilization, drying under reduced pressure, spray drying, ball drying or the like.

The process steps in the second process of the present invention are illustrated below.

Process Step ($A_2$)

As an extract solution or water washings used in step ($A_2$) can be employed the same materials as mentioned in step ($A_1$) of the first process. The concentration of protein contained in the extract solution or water washings is adjusted to preferably 1–10 mg/ml, more preferably 2–8 mg/ml to form a calcium phosphate gel.

The concentrations of calcium and phosphate ions to be contained in the extract solution or water washings for the formation of a calcium phosphate gel correlate with the concentration of protein contained in the solution and the adjustment is required. In general, a compound serving as a source of calcium ion is added in such a calcium ion concentration as to give 10–200%, preferably 20–120% of the concentration of protein contained in the solution and a compound serving as a source of phosphate ion is added in such a phosphate ion concentration as to give 20–100%, preferably 30–100% of the calcium ion concentration, thereby forming a calcium phosphate gel on which the amylase inhibitor and other proteins are adsorbed smoothly. The calcium phosphate gel thus formed is separated and recovered from the solution.

As the compounds serving as sources of calcium and phosphate ions can be used similar compounds as used in the first process of the invention. The process step ($A_2$) is preferably performed at a pH of the solution of 5–8, preferably 6–7 at a temperature of 30°–90° C., preferably 40°–60° C.

Process Step ($B_2$)

In this step ($B_2$), the methods for solubilizing the amylase inhibitor in water from the insoluble complex (calcium phosphate gel containing the amylase inhibitor adsorbed thereon) include (i) the method of adding acids, (ii) the method of adding water-soluble salts and (iii) the method of heating.

In the method (i), the acids used include inorganic acids such as hydrochloric acid, sulfuric acid and organic acids such as acetic acid, lactic acid. At that time, the pH is preferably adjusted to not greater than 4, specifically 1–3. In the method (ii), the water-soluble salts used include those having a strong affinity with a calcium ion, e.g. sodium sulfate, potassium sulfate, ammonium sulfate, sodium phosphate, potassium phosphate and ammonium phosphate. Preferably, the amount of water-soluble salts used is about 1–10% by weight of the solution in which insoluble complex is dispersed. In the method (iii), it is preferable that the insoluble complex is dispersed in a sufficient amount of water and a dispersion is heated at 50°–90° C., preferably 70°–85° C.

The aqueous solution containing a solubilized amylase inhibitor obtained in step ($B_2$) may be subjected, if necessary, to centrifugation, filtration or the like to separate water-insoluble solid forms and thereafter the aqueous solution containing the amylase inhibitor is treated in step ($C_2$) to modify soluble impure proteins and other impurities to their insoluble solids which are then separated and removed from the solution. The aqueous solution containing the amylase inhibitor obtained in step ($B_2$) contains, in addition to the amylase inhibitor, enzyme proteins such as α-amylase, β-amylase, soluble impure proteins such as part of albumin present in unstable state, globulin or the like, soluble saccharides, inorganic salts dyes or the like. Those impure proteins and other impurities are removed in step ($C_2$).

Suitable treatments for removal of impurities employed in step ($C_2$) can include:

(i) heating the aqueous solution containing the amylase inhibitor obtained in step ($B_2$) at a temperature of 70°–90° C., preferably 80°–90° C., thereby modifying heat unstable impure proteins to insoluble solids and removing said solids by sedimentation;

(ii) adjusting the pH of the aqueous solution containing the amylase inhibitor obtained in step ($B_2$) to not greater than 4, preferably 1.5–3, allowing to stand for a certain time followed by neutralization and removing impurities such as impure proteins which are precipitating as insoluble solids.

Process Step ($D_2$)

The aqueous solution containing a solubilized amylase inhibitor obtained in step ($C_2$) may be subjected, if necessary, to centrifugation, filtration or the like to remove water-insoluble impurities, and further subjected, if necessary, to microbial elimination, sterilization heating, alcohol sterilization, filtration for microbial elimination), cation exchanger (e.g. polymer cation exchange resins, aluminum silicate or the like), desalting or concentration, and thereafter drying to produce the desired amylase inhibitor in solid form such as powders. The drying treatment may be carried out by any suitable method such as lyophilization, drying under reduced pressure, spray drying, ball drying or the like.

By the first and second processes of the present invention as mentioned above, amylase inhibitors having a very high amylase inhibitory activity but no or very little trypsin inhibitory activity can be produced in economy and in high yields with a simple operation, while controlling occurrence of loss even when the amount of the solution treated is much. The amylase inhibitors produced by those processes have a high inhibitory activity against the amylase contained in pancreatic juice, is effective for the inhibition of insulin secretion and also is highly effective in inhibiting digestion of the cooked starch such as cooked rice or in inhibiting the hydrolysis to glucose.

The amylase inhibitors produced by the present processes can be used alone or in combination with conventional carriers or adjuvants for pharmaceutical preparation in the form of a liquid preparation or a solid preparation such as granules and tablets as an agent for inhibiting an increase in blood glucose level or an agent for controlling an insulin secretion. In addition, the amylase inhibitor can be used as food additives, particularly for carbohydrate foods rich in starch such as bread and cookie or as additives for tea, soup, seasoned fish meal and spread such as butter and jam. The amount of the amylase inhibitor administered to humans or added to foods can be adequately controlled depending upon conditions and symptoms of the subject to be administered or nature and quantity of foods to be ingested. For example, the amount of the amylase inhibitor ingested when added to foods may be in the range of about 0.1 to 20 g, preferably about 0.4 to 8 g per meal.

The invention is further illustrated by the following examples in which the following procedure is used to determine an inhibitory activity of the products against human pancreatic amylase.

Determination of Amylase Inhibitory Activity

An aqueous sample solution and human pancreatic amylase were added to 20 mM piperazine-N,N'-bis(2-ethanesulfonate) buffer (pH 6.9) containing 50 mM NaCl, 5 mM $CaCl_2$ and 0.04% egg white albumin. The mixture was allowed to stand at 37° C. for 30 min. and then mixed with 0.5 ml of a 1.5% soluble starch solution at pH 6.9. The resulting solution was allowed to react by maintaining at 37° C. for 10 min. followed by addition of 2.5 ml of a reaction terminator solution (0.08M HCl, 0.4M acetic acid). To 0.2 ml of the reaction mixture was added 2.5 ml of an iodine solution (0.05% KI, 0.005% iodine) and the mixture was measured for absorbancy at 660 nm. The amylase was used in an amount sufficient to reduce the absorbancy by 80% when no sample solution was contained and the amount of the amylase inhibitor sufficient to inhibit the amylase activity by 50% was taken as 1 amylase inhibitory unit (U).

EXAMPLE 1

To 130 kg of wheat flour were added 70 liters of water and the mixture was kneaded to prepare a dough. The dough was washed with 1200 liters of water to recover 65 kg of gluten and 80 kg of wheat starch. At that time, 1000 liters of waste water washings produced. The waste water washings were heated at 80° C. for 15 minutes, by which water-soluble, impure proteins and other impurities were modified to their water-insoluble forms which were precipitated. The precipitates were removed using a De Laval centrifuge to give 960 liters of a supernatant.

To the supernatant were added calcium chloride and disodium hydrogenphosphate so as to give 3000 ppm of a calcium ion concentration (100% of protein concentration) and 2000 ppm of a phosphate ion concentration, respectively and the mixture was reacted at 40° C. for 2 hrs. A water-insoluble calcium phosphate gel producing at this time was recovered by centrifugation to obtain 80 kg.

The calcium phosphate gel was dispersed with 120 liters of water and the dispersion was adjusted with lactic acid to the pH of 3. After stirring for one hour, solids were removed by centrifugation to recover 160 liters of a supernatant.

The supernatant was concentrated using two sets of ultrafiltration membrance (FS10-Fs-FuSo382 manufactured by Dicel Co., Ltd.) and excess salts were desalted to obtain 20 liters of a concentrated solution.

To the concentrated solution was added ammonia to adjust the pH to 7.5. To the solution was added 5 liters of a cation exchange resin (Diaion HPK-55 manufactured by Mitsubishi Kasei K.K.) and stirred for one hour. The cation exchange resin was removed by filtration to recover the solution. The resultant solution was subjected to filtration for microbial elimination using a ceramic filter and lyophilized to 260 g of a dry powder (I). The dry powder (II) was determined for an amylase inhibitory activity according to the above-mentioned method. The result is shown in Table 1 below.

EXAMPLE 2

To 130 kg of wheat flour were added 70 liters of water and the mixture was kneaded to prepare a dough. The dough was washed with 1200 liters of water to recover 65 kg of gluten and 80 kg of wheat starch. At that time, 1000 liters of a waste water washings produced. The waste washings were adjusted with hydrochloric acid to the pH of 2.5, allowed to stand for one hour and adjusted with sodium hydroxide to the pH of 6.5, by which water-soluble impurity proteins and other impurities were precipitated. The precipitates were removed using a De Laval centrifuge to give 950 liters of a supernatant. To the supernatant were added calcium chloride and disodium phosphate so as to give 3000 ppm of a calcium ion concentration (80% of protein concentration) and 2000 ppm of a phosphate ion concentration, respectively and the mixture was reacted at 40° C. for 2 hrs. A water-insoluble calcium phosphate gel producing at this time was recovered by centrifugation to obtain 80 kg.

The calcium phosphate gel was dispersed with 130 liters of water, 10 kg of ammonium sulfate was added and stirring was continued for 2 hrs. The solids were removed using a filter press to recover 170 liters of a supernatant.

The supernatant was subjected to the same concentration and desalting treatment as used in Example 1 to obtain 20 liters of a concentrated solution. The concentrated solution was subjected to the same cation exchange treatment and filtration for microbial elimination as used in Example 1 and the resulting solution was lyophilized to 250 g of a dry powder (II). The dry powder (II) was determined for an amylase inhibitory activity according to the above-mentioned method. The result is shown in Table 1 below.

EXAMPLE 3

To 130 kg of wheat flour were added 70 liters of water and the mixture was kneaded to prepare a dough. The dough was washed with 1200 liters of water to recover 65 kg of gluten and 80 kg of wheat starch. At that time, 1000 liters of waste water washings were produced. To the waste water washings were added calcium chloride and disodium phosphate so as to give 3000 ppm of a calcium ion concentration (70% of a protein concentration in the solution) and 2000 ppm of a phosphate ion concentration, respectively and the mixture was reacted at 37° C. for 2 hrs (pH 6.5). A water-insoluble calcium phosphate gel produced at this time was separated and removed using a De Laval centrifuge to obtain 120 kg.

To the calcium phosphate gel were added 200 liters of water, 2 kg of a filter medium (Celite) and 10 kg of ammonium sulfate, the mixture was stirred for 2 hrs and the solids were removed using a filter press to recover 180 liters of the solution.

The solution thus recovered was heated at 80° C. for 15 minutes, by which water-soluble, impure proteins and other impurities were modified to water-insoluble forms which were precipitated. The precipitates were separated and removed using a De Laval centrifuge to give 160 liters of a supernatant.

The supernatant was subjected to the same concentration and desalting treatment as used in Example 1 to obtain 20 liters of a concentrated solution. The concentrated solution was subjected to the same cation exchange treatment and filtration for microbial elimination as used in Example 1 and the resulting solution was lyophilized to 230 g of a dry powder (III). The dry powder (III) was determined for an amylase inhibitory activity according to the above-mentioned method. The result is shown in Table 1 below.

REFERENCE EXAMPLE

Preparation of the amylase inhibitor according to the process of Japanese Patent Kokai Hei 5-301898 (corresponding to EPA 0567088 A2)

To 130 kg of wheat flour was added 70 liters of water and the mixture was kneaded to form a dough. The dough was washed with 1200 liters of water to recover 65 kg of gluten and 80 kg of wheat starch. At this stage, 1000 liters of waste water washings produced. The pH of the waste water washings was adjusted with hydrochloric acid to 3 and after allowing to stand for 30 min., adjusted with ammonia to 6.5, by which insoluble matters were precipitated. The precipitates were removed to recover 850 liters of a supernatant.

To the supernatant was added 300 ppm of sodium alginate. The mixture was adjusted to pH 4.2 and stirred for 30 min., thus forming water-insoluble matters. They were recovered using a De Laval centrifuge. The recovered mass was dispersed in 10 times amount of water. The dispersion was mixed with 0.76 kg of calcium chloride, thoroughly stirred, adjusted with ammonia to pH 8.5 and allowed to stand for one hour. The solids were separated and removed using a De Laval centrifuge to recover 100 liters of a supernatant.

The supernatant thus recovered was neutralized with hydrochloric acid, and the neutralized solution was heated at 80° C. for 30 min. Insoluble matters thus formed were separated by a De Laval centrifuge to recover a supernatant. The supernatant was concentrated using a ultrafiltration membrane (manufactured by Nitto Denko K.K.; NTU-3250CIR (20000 Dalton cut off)), while removing excess calcium salt to give 23 liters of a concentrated solution. The protein concentration in the concentrated solution was found to be 25 mg/ml.

23 liters of the concentrated solution were adjusted with ammonia to pH 7.5 and passed through a column (900 mm in length, 200 mm in inner diameter) in which 28 liters of a cation exchange resin (Diaion HPK-55 manufactured by Mitsubishi Kasei K.K.) has been packed at a flow rate of 1 lit./min. Fractions not adsorbed on and eluted from the cation exchange resin were collected.

The eluted fractions were filtered through a ceramic filter for elimination of microbials and then lyophilized to give 230 g of dry powder (V). The dry powder was determined for an amylase inhibitory activity. The result is shown in Table 1 below.

TABLE 1

|  | Amount recovered (g/kg of wheat flour) | Amylase inhibitory activity (unit/mg) |
|---|---|---|
| Dry powder (I) of Example 1 | 2.0 | 8200 |
| Dry powder (II) of Example 2 | 1.9 | 8200 |
| Dry powder (III) of Example 3 | 1.8 | 12000 |
| Dry powder (V) of Reference Example | 1.8 | 8000 |

The results shown in Table 1 reveal that the processes mentioned in Examples 1 to 3 can produce economically the amylase inhibitors having higher amylase inhibitory activity.

Industrial Application of the Invention

The process of the invention can overcome the difficulty in mass treatment of the extract solution and waste water washings encountered hitherto and can produce the desired amylase inhibitors in economy and high yield with good operability, while controlling occurrence of loss even when the amount of treatment is much. The manufacturing cost by the present processes is about a half of that by the process of Japanese Patent Kokai Hei 5-301898 (corresponding to EPA 0567088 A2). The amylase inhibitors produced by the present processes have a high inhibitory activity against the amylase contained in the pancreatic juice and thus can effectively inhibit a secretion of insulin, which are useful in the prophylaxis and treatment of diseases such as hyperglycemia, diabetes, hyperlipemia, arteriosclerosis and obesity.

Further, the amylase inhibitors produced by the present processes are associated with no adverse reactions such as diarrhea and nausea when ingested and are pleasant to the palate and easily ingested.

What is claimed is:

1. A process of producing an amylase inhibitor comprising the steps of:
   ($A_1$) treating an amylase inhibitor-containing solution extracted from wheat, wheat flour or wheat gluten with water, a dilute acid, a dilute alkali or an aqueous alcohol or treating amylase inhibitor-containing waste water washings discharged during the recovery of starch and/or gluten from wheat flour, to modify soluble impure proteins and other impurities contained therein to their insoluble solid forms, and subsequently separating and removing the solid forms;
   ($B_1$) adding a calcium ion and a phosphate ion to the extract solution or the waste water washings after removal of impurities obtained in step ($A_1$) to form an insoluble calcium phosphate gel while adsorbing the amylase inhibitor on the calcium phosphate gel, and subsequently separating and recovering the calcium phosphate gel containing the amylase inhibitor adsorbed thereon;
   ($C_1$) solubilizing the amylase inhibitor in water from said insoluble calcium phosphate gel to form a solution containing the amylase inhibitor; and
   ($D_1$) recovering the amylase inhibitor from the solution.

2. A process of claim 1 wherein the treatments for removal of impurities in step ($A_1$) include (i) heating the extract solution or waste water washings at a temperature of 70°–90° C., thereby modifying heat unstable impure proteins and other impurities to their insoluble solid forms and removing said solid forms by sedimentation; (ii) adjusting the pH of the extract solution or waste water washings to not greater than 4, followed by neutralization and removing impurities which are precipitating as insoluble solids; and (iii) combination of (i) and (ii).

3. A process of claim 1 wherein the formation of the calcium phosphate gel in step ($B_1$) is carried out in a concentration of calcium ion in the solution constituting 10–200% by weight of a protein concentration in the solution and a concentration of phosphate ion constituting 20–100% by weight of the calcium ion concentration, at a temperature of 30°–90° C. and at a pH of 5–8.

4. A process of producing an amylase inhibitor comprising the steps of:
   ($A_2$) adding a calcium ion and a phosphate ion to an amylase inhibitor-containing solution extracted from wheat, wheat flour or wheat gluten with water, a dilute acid, a dilute alkali or an aqueous alcohol, or to amylase inhibitor-containing water washings discharged during the recovery of starch and/or gluten from wheat flour to form a calcium phosphate gel while adsorbing the amylase inhibitor on the calcium phosphate gel, and subsequently separating and recovering the calcium phosphate gel containing the amylase inhibitor adsorbed thereon;
   ($B_2$) solubilizing the amylase inhibitor in water from said calcium phosphate gel to form a solution containing the amylase inhibitor; and
   ($C_2$) treating the amylase inhibitor-containing solution obtained in step ($B_2$) to modify soluble impure proteins and other impurities contained therein to their insoluble solid forms, and subsequently separating and removing said solid forms;
   ($D_2$) recovering the amylase inhibitor from the solution.

5. A process of claim 4 wherein the formation of the calcium phosphate gel in step ($A_2$) is carried out in a concentration of calcium ion in the solution constituting 10-200% by weight of a protein concentration in the solution and a concentration of phosphate ion constituting 20-100% by weight of the calcium ion concentration, at a temperature of 30°-90° C. and a pH of 5-8.

6. A process of claim 4 wherein the treatments for removal of impurities in step ($C_2$) include (i) heating the amylase inhibitor-containing solution obtained in step ($B_2$) at a temperature of 70°-90° C. thereby modifying heat unstable impure proteins and other impurities to their insoluble solid forms and removing said solid forms by sedimentation; (ii) adjusting the pH of the amylase inhibitor containing solution obtained in step ($B_2$) to not greater than 4, followed by neutralization and removing impurities which are precipitating as insoluble solids; and (iii) combination of (i) and (ii).

* * * * *